United States Patent [19]
Chabardes et al.

[11] Patent Number: 5,874,636
[45] Date of Patent: Feb. 23, 1999

[54] PROCESS FOR THE PREPARATION OF TERPENIC KETONES

[75] Inventors: Pierre Chabardes; Claude Mercier, both of Lyons, France

[73] Assignee: Rhone-Poulenc Rorer S.A., Antony, France

[21] Appl. No.: 864,385

[22] Filed: Apr. 6, 1992

Related U.S. Application Data

[63] Continuation of Ser. No. 652,049, Feb. 8, 1991, abandoned.

[30] Foreign Application Priority Data

Feb. 8, 1990 [FR] France .................................. 90 01441

[51] Int. Cl.$^6$ .................................................. C07C 45/65
[52] U.S. Cl. ........................ 568/388; 568/395; 568/346; 560/174
[58] Field of Search .................................... 568/346, 388, 568/395; 560/174

[56] References Cited

U.S. PATENT DOCUMENTS

| | | | |
|---|---|---|---|
| 2,658,911 | 11/1953 | Kimel | 568/388 |
| 3,387,003 | 6/1968 | Mortel et al. | 568/388 |
| 3,609,192 | 9/1971 | Hoffman et al. | 568/388 |
| 3,723,500 | 3/1973 | Coulson | 560/174 |
| 3,914,289 | 10/1975 | Akutagawa et al. | 560/174 |
| 3,981,891 | 9/1976 | Celli et al. | 568/346 |
| 3,998,872 | 12/1976 | Symon et al. | 568/395 |
| 4,092,362 | 5/1978 | Celli | 568/346 |
| 4,460,786 | 7/1984 | Morel | 568/395 |
| 4,496,766 | 1/1985 | Tsuji et al. | 560/174 |
| 4,575,570 | 3/1986 | Katuoka et al. | 560/174 |
| 4,621,165 | 11/1986 | Moul | 568/395 |

FOREIGN PATENT DOCUMENTS

| 1132659 | 3/1957 | France | 568/388 |
|---|---|---|---|

*Primary Examiner*—James H. Reamer
*Attorney, Agent, or Firm*—Finnegan, Henderson, Farabow, Garrett & Dunner, L.L.P.

[57] ABSTRACT

The present invention relates to a process for the preparation of terpenic ketones, which comprises reacting a 1,3-butadiene derivative with a β-keto ester followed by decarbalkoxylation of the product.

21 Claims, No Drawings

PROCESS FOR THE PREPARATION OF TERPENIC KETONES

This application is a continuation of prior application Ser. No. 07/652,049 filed Feb. 8, 1991 now abandoned.

BACKGROUND OF THE INVENTION

The present invention relates to a process for the preparation of terpenic ketones. More particularly, it relates to the preparation of terpenic ketones from 1,3-butadiene which may be substituted on the carbon atom 2 by a hydrocarbon chain, preferrably a polyene chain and more preferably an isoprene chain. The terpenic polyene ketones are of the following general formula:

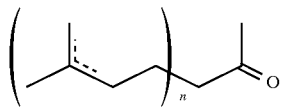

in which n is an integer from 1 to 4.

European Patent 33,771 describes the condensation reaction of a compound having an activated carbon atom with a conjugated substituted diene. The conjugated substituted diene may be a 1,3-butadiene substituted on the carbon atom 2 by a hydrocarbon chain. The compounds having an activated carbon atom may be selected, for example, from aldehydes, ketones, esters, sulphonic esters, nitrate derivatives, cyano derivatives and amides. The products of the condensation reaction are compounds in which the activated carbon atom is substituted with the conjugated substituted diene. These products serve as precursors for vitamins A and E or can be used in perfumes.

The decarboxylation of β-keto esters by means of a medium composed of water and dimethyl sulphoxide is described by Krapcho et al., J. Org. Chem., 43, pages 143, (1978). However, this paper does not describe the decarboxylation of β-keto esters substituted by a terpene group such as isoprene. The decarboxylation reaction described in this paper suffers from the use of a solvent such as dimethyl sulphoxide which the industry tries to avoid because it is expensive and hazardous.

J. M. Derfer et al. (Kirk Othmer, 22, page 731) describe the preparation of geranylacetone, which is a terpenic ketone, by transesterification of linalool with ethyl acetoacetate according to the Carroll reaction by the elimination of carbon dioxide. This reaction, however, is specific for linalool. Because linalool is an expensive raw material, there has been long-felt need for a means of access to vitamins which avoid the use of linalool as a starting material.

SUMMARY OF THE INVENTION

It is an object of the present invention to provide a process for the economical synthesis of terpene ketones. Terpenic ketones are known to be precursors in the synthesis of vitamins A and E and are useable in perfumes.

The object of this invention is accomplished by a process for the preparation of terpenic ketone comprising the steps of:

reacting a butadiene derivative of the formula:

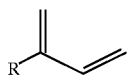

wherein R is a hydrocarbon radical having 1 to 20 carbon atoms.

with a β-keto ester; and causing the product of that reaction to undergo decarbalkoxylation.

DETAILED DESCRIPTION OF THE INVENTION

The present invention is a process for the preparation of terpenic ketones, wherein a derivative of 1,3-butadiene of the formula:

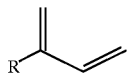

in which R represents a hydrocarbon radical having 1–20 carbon atoms is reacted with β-keto ester followed by decarbalkoxylation of the product.

The term 1,3-butadiene derivative is meant to emcompass hydrocarbon compounds which have at least two double bonds in a 1,3 relationship. Preferably, R in the above formula is polyene radical and more preferably a polyisoprene radical. Therefore, the preferred 1,3-butadiene derivatives are compounds of the following formula (I):

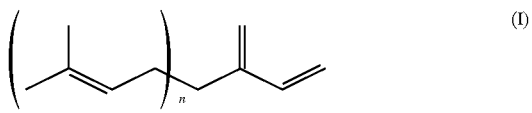

in which n is an integer equal to or greater than 0 and smaller than or equal to 3. Particularly preferred compounds of formula (I) are:

myrcene (7-methyl-3-methylene-1,6-octadiene)

isoprene (2-methyl-1,3-butadiene)

β-farnesene

The β-keto esters employed in the present invention are preferably alkyl acetoacetates of the following formula (II):

$$R—O_2C—CH_2—CO—CH_3 \qquad (II)$$

in which $R_1$ represents a hydrocarbon radical having 1 to 12 carbon atoms, preferably in the form of a linear or branched alkyl or alkenyl chain or of an optionally substituted aromatic radical. Preferred alkyl acetoacetates of the formula (II) are those in which $R_1$ represents an alkyl group having 1 to 4 carbon atoms, and particularly preferred is methyl acetoacetate.

The addition reaction can be carried out in the presence of a catalyst, preferably a rhodium-based catalyst. An example of this addition reaction is described in U.S. Pat. No. 4,460,786; the disclosure of which is incorporated herein by reference. This preferred catalyst may be selected from the salts, oxides and complexes of rhodium. According to a preferred embodiment of the process-of the invention, the rhodium catalyst is selected from the inorganic salts, organic salts and complexes of rhodium, such as, e.g., $RhCl_3$, $RhBr_3$, $Rh_2$, $Rh_2O_3$, $Rh(NO_3)_3$, $Rh(CH_3COO)_3$, $Rh(CH_3COCHCOCH_3)_3$, $[RhCl(1,5-cyclooctadiene)]_2$, $[RhCl(CO)_2]_2$, $RhCl_3(C_2H_5NH_2)_3$, and $Rh_2(SO_4)_3$. Particularly preferred are $RhCl_3$ and $[RhCl(1,5-cyclooctadiene)]_2$.

If appropriate, the catalyst reaction can be carried out in the presence of an added ligand. Preferred ligands are phosphiie ligands; more preferred are those having the formula (III):

in which:

Ar$_1$, Ar$_2$ and Ar$_3$ are identical or different and each represents a radical selected from phenylene radicals and naphthylene radicals; these radicals may be substituted or unsubstituted, M is an inorganic or organic cationic radical preferably selected in such a way that the phosphine of the formula (III) is soluble in water; and n$_1$, n$_2$ and n$_3$ are identical or different and are integers greater than or equal to 0 and smaller than or equal to 3, at least one being greater than or equal to 1.

The process according to the invention is preferably carried out by using at least one phosphine ligand of the formula (III) in which Ar$_1$, Ar$_2$ and Ar$_3$ are identical or different and each represents a phenylene radical. Particularly preferred are phosphine ligands which are soluble in an aqueous medium and in which the SO$_3$M groups are in the meta-position on the phenyl ring. Preferably, M is selected from the cations Na$^+$, K$^+$, Ca$^{2+}$, Ba$^{2+}$, NH$_4^+$ ions and quaternary ammonium ions such as the tetramethylammonium, tetrapropylammonium and tetrabutylammonium ions.

The numbers represented in formula (III) by n$_1$, n$_2$ and n$_3$ are preferably each equal to 1. The use of meta-trisulphonated triphenyl-phosphine is most preferred.

The quantity of rhodium or rhodium compound used is such that the molar concentration of elemental rhodium per litre of reaction solution ranges from about $10^{-4}$ to about 1. Preferably, it ranges from about 0.001 to about 0.5 moles of rhodium per litre of solution.

The quantity of phosphine used in a preferred embodiment is selected such that the molar ratio of trivalent phosphorus relative to rhodium ranges from about 0.1:1 to about 200:1. Preferably, the molar ratio of P$^{3+}$:Rh ranges from about 3:1 to about 100:1.

The general addition reaction is shown by the following reaction:

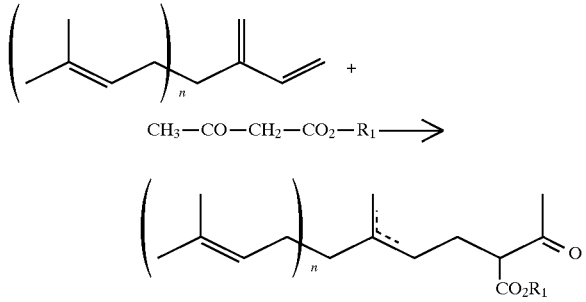

The ester produced is then contacted with water in such a way that decarbalkoxylation occurs. A surprising aspect of this invention is that with compounds of this type, polyene β-keto esters, it is not necessary to add a solvent or a decarbalkoxylating agent; water alone permits this reaction in the absence of any catalyst. This represents a considerable economic advantage in the industrial field. Additionally, there are no secondary products which are difficult to remove. The only by-products of the reaction are carbon dioxide and an alcohol of the formula ROH; both by-products are easily removed from the product mixture.

The ester used in the decarbalkoxylation reaction can be an isolated purified product or the crude product obtained directly from the addition reaction condensing the β-keto ester and the butadiene derivative. Advantageously, the decarbalkoxylation can be carried out in the same reaction vessel as the addition reaction.

The decarbalkoxylation reaction may be carried out in the vapour phase or liquid phase at a temperature ranging from about 130° C. to about 500° C. If the reaction is carried out in the vapour phase, the temperature preferably ranges from about 300° to about 500° C. and even more preferably from about 350° to about 400° C. If the reaction is carried out in the liquid phase, it is preferred to use a temperature ranging from about 180° to about 220° C. The reaction can also be carried out in a downward-flow phase over a bed of unreactive solid material such as quartz.

The decarbalkoxylation reaction can be carried out under atmospheric pressure, a reduced pressure or an elevated pressure. It is preferred to carry out the reaction under a pressure of less than 100 bar and particularly preferred under a pressure ranging from 1 to 20 bar. The temperature and pressure conditions can be adjusted by those skilled in the art according to the starting materials employed.

The polyene ketone derivatives obtained are synthesis intermediates, which are important in the vitamin and perfume industries. For example, the process of this invention can be used to make the following compounds:

geranylacetone,
methylheptenone,
farnesylacetone.

The present invention will be more completely described in, but is not limited to, the following examples. In the examples which follow, the compounds of general formulas (I) and (II) are represented by the following formulas:

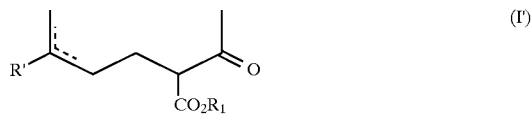

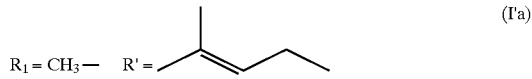

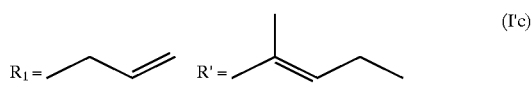

geranylacetone (II'a)
methylheptenone (II'b)

EXAMPLE 1

[RhCl(1,5-Cyclooctadiene)]$_2$, 150 mg (0.615 mmol of rhodium), sodium triphenylphosphine-trisulphonate 4.2 g (6.2 mmol of P$^{3+}$), Na$_2$CO$_3$, 0.1 g (~1 mmol) and water (70 ml) are introduced into a stainless steel autoclave previously purged with nitrogen. 34 g (250 mmol) Myrcene of 99% purity, and 34.8 g (300 mmol) methyl acetoacetate are then introduced into the autoclave.

The mixture is heated with stirring for 17 hours at 85° C. Thin-layer chromatography gives a conversion rate of about 100% with formation of the β-keto ester (I'a) in an equimolar exo/endo mixture as determined by $^1$H NMR.

The two-phase mixture (pale yellow organic phase and red-orange aqueous phase) is used in the decarboxylation step in the same autoclave and heated for 3 hours at 180° C. until the rise in pressure due to the evolution of gas ceases. The pressure is increased to 25 bar in a 750 ml reactor. The mixture is then cooled and degassed. The two phases are then separated. Analysis of the organic phase by thin-layer chromatography, gas chromatography and $^1$H NMR after extraction of the two-phase system gives complete conversion of the β-keto eters (I'a). An organic phase essentially containing the two isomers of geranylacetone II'a (exo and endo) is obtained: yield: 40.3 g. Distillation permits pure geranylacetone (2 isomers) to be isolated, yield: 33 g (b.p.$_1$ about 82° C.). The overall yield of distilled geranylacetone relative to the myrcene starting materials is 67.4%.

The leftover yellow-orange aqueous phase is homogeneous and contains 0.54 g/l of the soluble rhodium catalyst.

EXAMPLE 2

[RhCl(1,5-cyclooctadiene))]$_2$, 150 mg (0.615 mmol of rhodium), sodium triphenylphosphine-trisulphonate, 8.4 g (12.4 mmol of $P^{3+}$), $Na_2CO_3$, 0.1 g (~1 mmol) and water (80 ml) are introduced into a stainless steel autoclave previously purged with nitrogen. Myrcene of 78% purity (technical grade), 43.5 g (250 mmol) and methyl acetoacetate, 34.8 g (300 mmol) are then introduced into the autoclave.

The mixture is heated with stirring for 17 hours at 91° C. Thin-layer chromatography of the organic phase gives a conversion rate of about 100% of the myrcene, with formation of the β-keto esters (I'a) having an equimolar endo/exo mixture as determined by $^1$H NMR.

The two-phase mixture (pale yellow organic phase and red-orange aqueous phase) is used in the decarboxylation step in the same autoclave, and heated for 3 hours at 180° C. until the rise in pressure due to the evolution of gas ceases. The mixture is then cooled and degassed. Analysis by thin-layer chromatography (TLC), gas chromatography (GC) and $^1$H NMR after extraction of the two-phase system gives complete conversion of the β-keto ester (I'a). An organic phase essentially containing the two isomers of geranylacetone (II'a) (exo and endo) is isolated, yield: 48.7 g. Distillation permits isolation of a first fraction (b.p.$_1$ about 25°–30° C.) containing the inert $C_{10}$-hydrocarbons present in the technical grade myrcene (9.4 g) and a second fraction corresponding to pure geranylacetone (2 isomers), yield: 30.6 g (b.p. about 82° C.). The overall yield of distilled geranylacetone is 63%.

The remaining yellow-orange aqueous phase is homogeneous and contains the homogeneous soluble rhodium catalyst.

EXAMPLE 3

Quartz powder (10 ml) is placed in a tubular reactor of 18 mm diameter and preheated for 30 minutes at 350° C. under a nitrogen stream (3.5 l/hour). The β-keto ester I'a (mixture of the 2 isomers, 95% pure) is then injected by means of a pusher syringe at a rate of 10 ml h$^{-1}$, and softened water is injected by means of a second pusher syringe at 3.5 ml h$^{-1}$ (about 5 equivalents relative to the β-keto ester), giving a mean contact time of 3.8 seconds. A vapor phase reaction takes place. After 35 minutes, analysis of the two-phase condensate (colourless aqueous phase, yellow organic phase) by thin-layer chromatography, gas chromatography and $^1$H NMR shows the formation of geranylacetone at a conversion rate of the β-keto ester of 70%, a selectivity for geranylacetone of 85% and a productivity of 1.1 kg h$^{-1}$ l$^{-1}$.

EXAMPLE 4

The β-keto ester (I'a) 10 g (45% endo and 55% exo) is charged under nitrogen into a 100 ml three-necked flask surmounted by a distillation column and fitted with a thermometer, the reaction mass is rapidly heated to 170–180° C. with magnetic stirring, and water is then introduced at the rate of 1.2 ml/h into the reaction mass by means of a pusher syringe. The progress of the reaction is followed by gas chromatography using aliquot samples and by the evolution of $CO_2$. After 1 hour and 30 minutes, complete conversion is observed. Distillation provides a 92% yield of geranylacetone.

EXAMPLE 5

The apparatus described in Example 4 is charged under nitrogen with β-keto ester (I'b) 10 g (40% endo and 60% exo). The reaction mass heated to 180° C. Softened water (2.5 ml) is injected over 2 hours onto the heated reaction mass. This give's complete conversion as monitored by gas chromatography and $^1$H NMR analysis. After distillation (b.p. 69° C. at 15 mm Hg), methylheptenone (II'b) 6.1 g (89.7% yield), as identified by gas chromatography, $^1$H NMR and IR spectroscopy, is recovered.

EXAMPLE 6

The apparatus described in Example 3 is operated at 400° C. under a nitrogen stream (3.5 l h$^{-1}$ under standard temperature and pressure conditions). The β-keto ester (I'a) (96% purity, 55/45 mixture of the two endo/exo isomers) is injected by means of a pusher syringe at a rate of 10 ml h$^{-1}$ (36.5 mmol h$^{-1}$) and softened water is simultaneously injected by means of a second pusher syringe at 2.4 ml h$^{-1}$ (133.3 mmol h$^{-1}$, 3.65 equivalents), corresponding to a mean contact time of 4.6 seconds. After 40 minutes of reaction in the vapour phase, analysis of the two-phase condensate (1.3 ml of colourless aqueous phase and 3.90 g of yellow organic phase (after elimination of the light end fractions in a rotary evaporator) shows, by TLC, GC and $^1$H NMR, the formation of geranylacetone (II'a) at a conversion rate of the β-keto ester (I'a) of about 84% and a selectivity for geranylacetone of 85%.

EXAMPLE 7

The procedure of Example 6 using the apparatus described in Example 3 but operating at 450° C. is repeated. After a reaction time of 35 minutes, a two-phase condensate (1.2 ml of colourless aqueous phase and 4.38 g of yellow organic phase) is obtained. Analysis by TLC, GC and $^1$H NMR shows the formation of geranylacetone (II'a) at a conversion rate of the β-keto ester (I'a) of about 63% and a selectivity for geranylacetone of 73%.

EXAMPLE 8

Example 6 is repeated with an apparatus temperature of 400° C., but with a modified β-keto ester injection rate of 4.95 ml h$^{-1}$ (18.2 mmol h$^{-1}$). All other reaction conditions are the same, i.e. a ratio of 7.3 equivalents of water relative to the β-keto ester and a mean contact time of 4.8 seconds. After reacting for 1 hour and 5 minutes, a two-phase condensate containing 2.2 ml of colourless aqueous lower phase and 3.52 g of organic phase (after elimination of the light end fractions in a rotary evaporator) Ls obtained. The analysis of the organic phase (TLC, GC and $^1$H NMR) indicates complete conversion of the β-keto ester (I'a) and formation of geranylacetone (II'a) with a selectivity of 75% and a reaction productivity of 500 g/l per hour.

EXAMPLE 9

The apparatus described in Example 3 is operated, but at 250° C., and in accordance with a downward-flow fixed-bed technique (cf. Technique de l'Ingenieur, Vol. J4, "Geni. Chimique", 1965, paragraphs 2–4, specifically incorporated by reference herein). Under nitrogen (3.5 l h$^{-1}$), the β-keto ester (I'a) of Example 6 is injected at a rate of 4.95 ml h$^{-1}$ (18.2 mmol h$^{-1}$) injected, and softened water is simultaneously injected by means of a second pusher syringe at 2.4 ml h$^{-1}$ (133.3 mmol, 7.3 equivalents). After reacting for 55 minutes, a two-phase condensate with 1.9 ml of colourless aqueous phase and 3.93 g of pale yellow organic phase (after elimination of the light end fractions in a rotary evaporator) is obtained. Analysis of the recovered product by TLC, GC and $^1$H NMR indicates a conversion rate of the β-keto ester of about 25% and formation of geranylacetone (II'a) with a selectivity of 88%.

EXAMPLE 10

Example 4 is repeated, but the reaction is carried out at atmospheric pressure in a 300 ml Sotelem stainless steel autoclave fitted with a Ruchton turbine which allows excellent transfer. The autoclave was heated to 200° C. water injected into the reaction mass by means of a Hazel pusher syringe. The methanol produced by the reaction is recovered in a trap after distillation and a hydraulic precision gas counter being used to measure the volume of $CO_2$ released.

Under a nitrogen atmosphere, the autoclave is charged with the β-keto ester of Example 6 (96% pure) 131.25 g (0.5 mol) and heated to 2000° C. while stirring at 2000 rpm. Softened water is then injected at 1 ml h$^{-1}$. The progress of the reaction is monitored by the volume of $CO_2$ released. After 1 hour and 5 minutes, 15.5 ml of water (1.72 equivalents relative to β-keto ester introduced) have been injected, and 11.5 l of $CO_2$ have been released when the evolution of gas caused by the reaction has ceased. After cooling, 97.2 g (115 ml) of the reaction mass are isolated. Subsequent analysis (TLC, GC and $^1$H NMR) indicates complete conversion of the β-keto ester (I'a) to a 94% yield of geranylacetone (IIa) and 95% purity of the crude product. The reaction mass is then distilled. The colourless distillate (24 ml) contains predominantly methanol (identified by GC.) and excess water. This allows easy recovery of the methanol by simple distillation.

EXAMPLE 11

The β-keto ester (I'a), 10 g (38.1 mmol, purity 96%) and water, 2 g (111.1 mmol, 2.92 equivalents relative to the β-keto ester), are introduced into a 125 ml stainless steel autoclave previously purged with nitrogen. The mixture is then heated at 220° C. with stirring until the rise in pressure due to the gas evolution ceases, (after about 0.5 hour, the pressure reaching 24 bar). The mixture is then cooled and degassed. Analysis after decantation of the two-phase system by TLC, GC and $^1$H NMR indicates complete conversion of the β-keto ester. The organic phase essentially contains the two isomers of geranylacetone (II'a) obtained in a yield of 91% at a purity of 93%.

EXAMPLES 12 TO 16

The procedure of Example 11 is followed as in Example 11, but at variable temperatures. Table 1 below summarizes the results:

TABLE 1

| EXAMPLE NO. | REACTION TEMPERATURE (°C.) | REACTION TIME | MAXIMUM PRESSURE (bar) | RESULTS CONVERSION RATE (β-KETO ESTER) (I'a) | YIELD (GERANYL-ACETONE) (II'a) |
|---|---|---|---|---|---|
| 12 | 180° C. | 2 hours | 19 bar | 100 | 91 |
| 13 | 150° C. | 3 hours | 5 bar | 34 | 95 |
| 14 | 250° C. | 30 minutes | 25 bar | 100 | 90 |
| 15 | 295° C. | 30 minutes | 29 bar | 100 | 89 |
| 16 | 165° C. | 6 hours | 11 bar | 100 | 91 |

EXAMPLE 17

21.5 millimol of the following β-keto ester

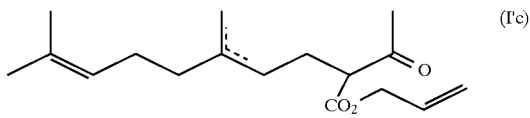

(6.8 g, purity about 90%) and 3 equivalents of water relative to the β-keto ester are introduced into a 125 ml stainless steel autoclave previously purged with nitrogen. The mixture is then heated at 180° C. for 3 hours and 30 minutes (until there is no further increase in pressure). After cooling and degassing, analysis of the two-phase system after decantation by TLC, GC and $^1$H NMR indicates a conversion rate of 97% of the allyl β-keto ester (I'c) and the formation of geranylacetone (II'a) in a yield of 89% and a purity of 91%.

EXAMPLE 18

Example 12 of French Patent 2,486,525 (commonly assigned with the present application) relating to the addition of ethyl acetoacetate to isoprene is repeated, but the β-keto ester (I'd) is not isolated. The addition reaction is directly followed by decarbethoxylation in the same autoclave, which permits a "one-pot" reaction with isoprene to give methylheptenone without isolation of the intermediates.

In more detail, [RhCl(1,5-cyclooctadiene)]₂, 34 mg (0.14 mmol of rhodium), sodium triphenylphosphine-trisulphonate, 0.3 g (0.14 mmol of $P^{3+}$), $Na_2CO_3$ 80 mg (0.73 mmol) and water (30 ml) are introduced into a 125 ml stainless steel autoclave previously purged with nitrogen. Isoprene, 6.9 g (102 mmol) and ethyl acetoacetate, 16.2 g (125 mmol) are then introduced. The mixture is heated for 4 hours at 100° C. with stirring, and this is directly followed by heating for 3 hours at 220° C. during which the pressure increases to 37 bar. After the second heating, the resulting two-phase system is cooled, degassed and decanted. Analysis of the organic phase by TLC, GC and ¹H NMR indicates complete conversion of the isoprene and formation of the methylheptenone (II'b) in 71% yield (based on isoprene).

EXAMPLE 19

The reaction apparatus used in this example consists of a 100 ml three-necked flask with magnetic stirrer, a monoblock Vigreux column, a receiver flask connected to a water cell surmounted by a graduated tube for measuring the volume of $CO_2$ evolved, a Hazel pusher syringe with a stainless steel dipping needle for introduction of the water and heating by a controlled oil bath.

The flask is charged under nitrogen with 31.8 millimol of β-keto ester (I'a) 10 g (31.8 mmol, purity 96%), and the reaction mass is rapidly heated with magnetic stirring to 160° C. Softened water is then injected at a rate of 1.2 ml h⁻¹ into the reaction mass by means of a pusher syringe. The progress of the reaction is monitored by the evolution of $CO_2$. After 1 hour and 30 minutes, 600 ml of $CO_2$ have formed and analysis by GC, ¹H NMR and TLC shows a conversion rate of 60% of the β-keto ester and the formation of geranylacetone in 95% yield.

EXAMPLES 20 TO 21

The procedure of Example 19 is followed at variable temperatures. Table 2 below summarizes the results:

TABLE 2

| | | | RESULTS | |
|---|---|---|---|---|
| EXAMPLE NO. | REACTION TEMPERATURE (°C.) | REACTION TIME | Conversion Rate (β-Keto Ester) (I'a) | Yield (Geranyl-Acetone) (II'a) |
| 20 | 200° C. | 50 minutes | 100 | 93 |
| 21 | 220° C. | 1 hour | 100 | 91 |

EXAMPLE 22

This example illustrates how the process can advantageously be applied to the production of geranylacetone from commercial raw materials such as technical grade myrcene (purity about 75 to 80%). At the end of the condensation stage of methyl acetoacetate with technical myrcene according to French Patent 2,486,525, (commonly assigned with the present application), the operation can be carried out as follows rather than by the (direct) decarbomethoxylation illustrated in Example 4:

After the condensation reaction has stopped, the mixture is cooled to ambient temperature. The reactor content is taken off, and the reaction product which is in the organic phase is then isolated by separating by decantation the latter from the aqueous phase containing the catalyst, if necessary, by an extraction by means of a suitable solvent. The aqueous solution can be recycled into the reactor and used as a catalyst in a new reaction. The aqueous solution can also remain in the reactor, the organic products being taken off in this case directly by decantation.

The organic phase thus recovered constitutes the crude β-keto ester and contains (starting from technical grade myrcene of a purity of 78.2% of myrcene) 71.2% of β-keto ester, accompanied by essentially inert constituents of technical grade myrcene (such as limonene), excess methyl acetoacetate and about; 1% of water.

The procedure of Example 4 is then followed but using 10 g of the crude β-keto ester having a purity of 71.2% (28.25 mmol β-keto ester). After reacting for 1 hour at 210° C., the evolution of $CO_2$ ceases. Analysis of the crude reaction product indicates complete conversion of the β-keto ester and a 92% yield of geranylacetone having 79% purity. The crude reaction product may be distilled to first remove impurities. It is found that the first distillate contains the inert constituents of technical myrcene (limonene: b.p., at 760 mm Hg) excess methyl acetoacetate in addition to the methanol formed in the reaction.

We claim:

1. A process for the preparation of a terpenic ketone comprising the steps of:

reacting, in the presence of water, a butadiene derivative of the formula:

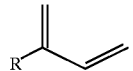

wherein R is a hydrocarbon radical having 1 to 20 carbon atoms with a β-keto ester; and causing the product of said reaction to undergo decarbalkoxylation in the presence of water without adding an additional component selected from the group consisting of a solvent and a decarbalkoxylating agent, wherein said reaction step and said decarbalkoxylation are carried out in the same reaction zone.

2. The process of claim 1 wherein said butadiene derivative is a polyene of formula (I):

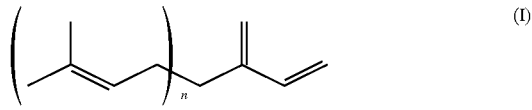

wherein n is an integer equal to or greater than 0 and smaller than or equal to 3.

3. The process of claim 2 wherein said polyene of formula. (I) is selected from myrcene, isoprene and β-farnesene.

4. The process of claim 2 wherein said β-keto ester is an alkyl acetoaccetate of the formula (II):

$$R-O_2C-CH_2-CO-CH_3 \quad (II)$$

wherein $R_1$ is a hydrocarbon radical having 1 to 12 carbon atoms.

5. The process of claim 4 wherein $R_1$ is an alkyl group having 1 to 4 carbon atoms.

6. The process of claim 5 wherein $R_1$ is methyl.

7. The process of claim 1 wherein said reaction step is further carried out in the presence of a ligand.

8. The process of claim 7 wherein said ligand is a phosphine ligand.

9. The process of claim 8 wherein said phosphine ligand is a phosphine ligand of the formula (III):

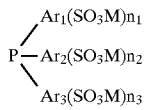

(III)

wherein:

Ar$_1$, Ar$_2$ and Ar$_3$ are identical or different and each represents a radical selected from phenylene radicals and naphthylene radicals, and wherein said radicals may be substituted or unsubstituted;

M is an inorganic or organic cationic radical; and n$_1$, n$_2$ and n$_3$ are identical or different and are integers greater than or equal to 0 and smaller than or equal to 3, at least one being greater than or equal to 1.

10. The process of claim 1 wherein said rhodium catalyst is RhCl$_3$ or [RhCl(1,5-cyclooctadiene)]$_2$.

11. The process of claim 9 wherein said rhodium catalyst is RhCl$_3$ or [RhCl(1,5-cyclooctadiene)]$_2$.

12. The process of claim 11 wherein said phosphine ligand is meta-trisulphonated triphenylphosphine.

13. The process of claim 4 wherein said decarbalkoxylation step is carried out at a temperature ranging from about 130° C. to about 500° C.

14. The process of claim 13 wherein said decarbalkoxylation is carried out in the liquid phase or the vapour phase.

15. The process of claim 14 wherein said decarbalkoxylation is carried out in the liquid phase at a temperature ranging from about 180° C. to about 220° C.

16. The process of claim 14 wherein said decarbalkoxylation is carried out in the vapour phase at a temperature ranging from about 300° C. to about 500° C.

17. The process of claim 16 wherein said decarbalkoxylation is carried out in the vapour phase at a temperature ranging from about 350° C. to about 400° C.

18. The process of claim 13 wherein said decarbalkoxylation is further carried out at a pressure of less than or equal to 100 bar.

19. The process of claim 12 wherein said 1,3-butadiene derivative is selected from myrcene, isoprene and β-farnesene and said β-keto ester is methylacetoacetate.

20. The process of claim 19 further comprising the step of recovering the catalyst.

21. The process of claim 9 further comprising the step of recovering the catalyst.

* * * * *